United States Patent
Ben Muvhar

(10) Patent No.: US 9,427,299 B2
(45) Date of Patent: Aug. 30, 2016

(54) FILTER APPARATUSES AND METHODS OF USING SAME

(75) Inventor: Shmuel Ben Muvhar, Paduel-Doar-Na Modiln (IL)

(73) Assignee: LithiBlock Ltd., Peduel (IL)

( * ) Notice: Subject to any disclaimer, the term of this patent is extended or adjusted under 35 U.S.C. 154(b) by 0 days.

(21) Appl. No.: 13/260,382

(22) PCT Filed: Mar. 25, 2010

(86) PCT No.: PCT/IL2010/000258
§ 371 (c)(1),
(2), (4) Date: Sep. 26, 2011

(87) PCT Pub. No.: WO2010/109467
PCT Pub. Date: Sep. 30, 2010

(65) Prior Publication Data
US 2012/0022550 A1    Jan. 26, 2012

(30) Foreign Application Priority Data
Mar. 25, 2009 (IL) .......................... 197800

(51) Int. Cl.
*A61F 2/01* (2006.01)
*A61F 2/04* (2013.01)

(52) U.S. Cl.
CPC ............ *A61F 2/01* (2013.01); *A61F 2002/018* (2013.01); *A61F 2002/041* (2013.01); *A61F 2002/048* (2013.01); *A61F 2210/0004* (2013.01); *A61F 2230/0006* (2013.01); *A61F 2230/008* (2013.01); *A61F 2230/0091* (2013.01); *A61F 2250/0067* (2013.01)

(58) Field of Classification Search
USPC ................ 606/151–158, 191, 198, 200, 213; 623/23.64–23.66, 23.69, 23.7
See application file for complete search history.

(56) References Cited

U.S. PATENT DOCUMENTS

| | | | |
|---|---|---|---|
| 5,925,062 A | 7/1999 | Purdy | |
| 6,342,059 B1 | 1/2002 | Chevillon et al. | |
| 6,616,680 B1 | 9/2003 | Thielen | |
| 6,623,507 B2 | 9/2003 | Saleh | |
| 7,524,319 B2 | 4/2009 | Dubrul | |
| 2002/0099437 A1* | 7/2002 | Anson et al. ................ | 623/1.15 |
| 2002/0193825 A1 | 12/2002 | McGuckin, Jr. et al. | |
| 2003/0040771 A1* | 2/2003 | Hyodoh et al. ............... | 606/200 |
| 2003/0057156 A1 | 3/2003 | Peterson et al. | |

(Continued)

FOREIGN PATENT DOCUMENTS

| | | |
|---|---|---|
| CN | 203424992 | 2/2014 |
| JP | 2005-508201 | 3/2005 |

(Continued)

OTHER PUBLICATIONS 7 9 1 Diameter, 7.9.4 Vessel Length. (2010). In P. A. Iaizzo (Ed.), Handbook of Cardiac Anatomy, Physiology, and Devices (2nd ed., p. 117-118). Springer Science & Business Media.*

(Continued)

*Primary Examiner* — Thomas McEvoy

(57) ABSTRACT

A filter device for implantation in a body lumen, comprising: a blocking section for filtering structures greater than a specified minimum size; and, an anchoring section for preventing unwanted movement of the filter device, wherein the filter device does not apply expansive radial force on a wall of the body lumen.

12 Claims, 12 Drawing Sheets

(56) References Cited

U.S. PATENT DOCUMENTS

| | | | |
|---|---|---|---|
| 2003/0078465 A1* | 4/2003 | Pai et al. | 600/16 |
| 2003/0163204 A1* | 8/2003 | Rix | 623/23.7 |
| 2004/0087997 A1 | 5/2004 | Brenneman | |
| 2007/0083230 A1 | 4/2007 | Javois | |
| 2007/0112372 A1 | 5/2007 | Sosnowski et al. | |
| 2007/0239199 A1* | 10/2007 | Jayaraman | 606/200 |
| 2008/0033457 A1* | 2/2008 | Francischelli et al. | 606/142 |
| 2008/0140216 A1 | 6/2008 | Ehrlinspiel et al. | |
| 2009/0254172 A1 | 10/2009 | Grewe | |

FOREIGN PATENT DOCUMENTS

| | | |
|---|---|---|
| JP | 2005-534429 | 11/2005 |
| WO | WO 02/071977 | 9/2002 |
| WO | WO 2004/012587 | 2/2004 |
| WO | WO 2006/131930 | 12/2006 |
| WO | WO 2010/109467 | 9/2010 |
| WO | WO 2011/143137 | 11/2011 |

OTHER PUBLICATIONS

International Preliminary Report on Patentability Dated Oct. 6, 2011 From the International Bureau of WIPO Re. Application No. PCT/IL2010/000258.

International Search Report and the Written Opinion Dated Aug. 24, 2010 From the International Searching Authority Re. Application No. PCT/IL2010/000258.

Office Action Dated Mar. 1, 2012 From the Israel Patent Office Re. Application No. 197800 and Its Translation Into English.

Elmunzer et al. "Percutaneous Cholecystostomy as a Bridge to Definitive Endoscopic Gallbaldder Stent Placement", Clinical Gastroenterology and Hepatology, 9: 18-20, 2011.

Itoi et al. "Endoscopic Gallbladder Drainage for Management of Acute Cholecystitis", Gastrointestinal Endoscopy, 71(6): 1038-1045, 2010.

Notice of Reason for Rejection Dated Nov. 29, 2013 From the Japanese Patent Office Re. Application No. 2012-501502 and Its Translation Into English.

Official Decision of Rejection Dated Aug. 1, 2014 From the Japanese Patent Office Re. Application No. 2012-501502 and Its Translation Into English.

International Search Report and the Written Opinion Dated Feb. 3, 2016 From the International Searching Authority Re. Application No. PCT/L2015/051051.

* cited by examiner

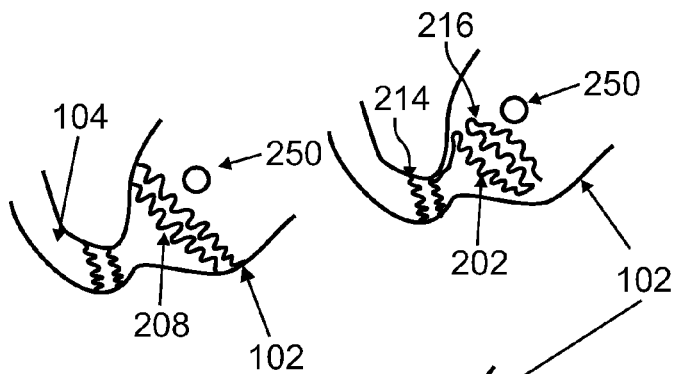
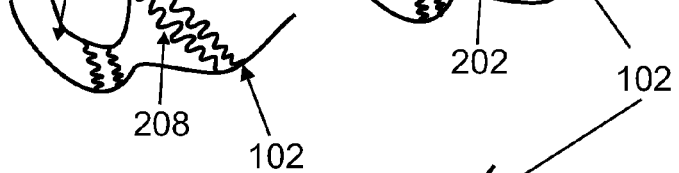
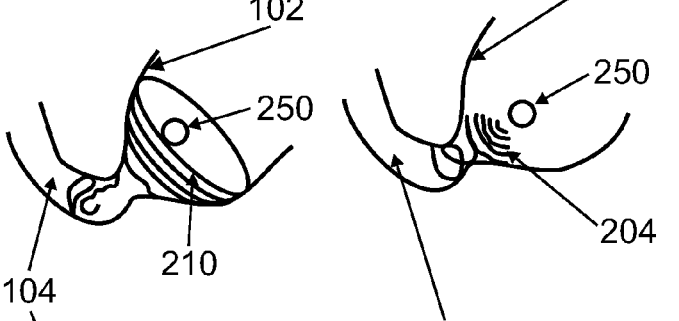
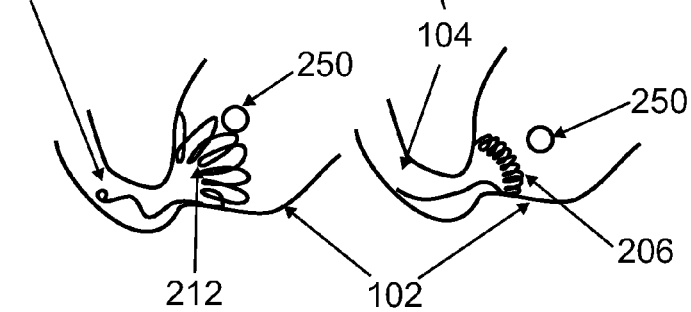
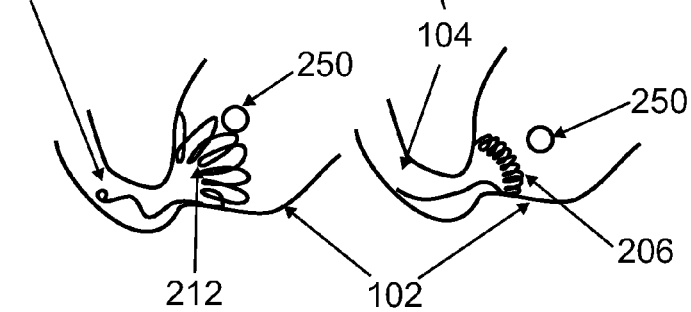

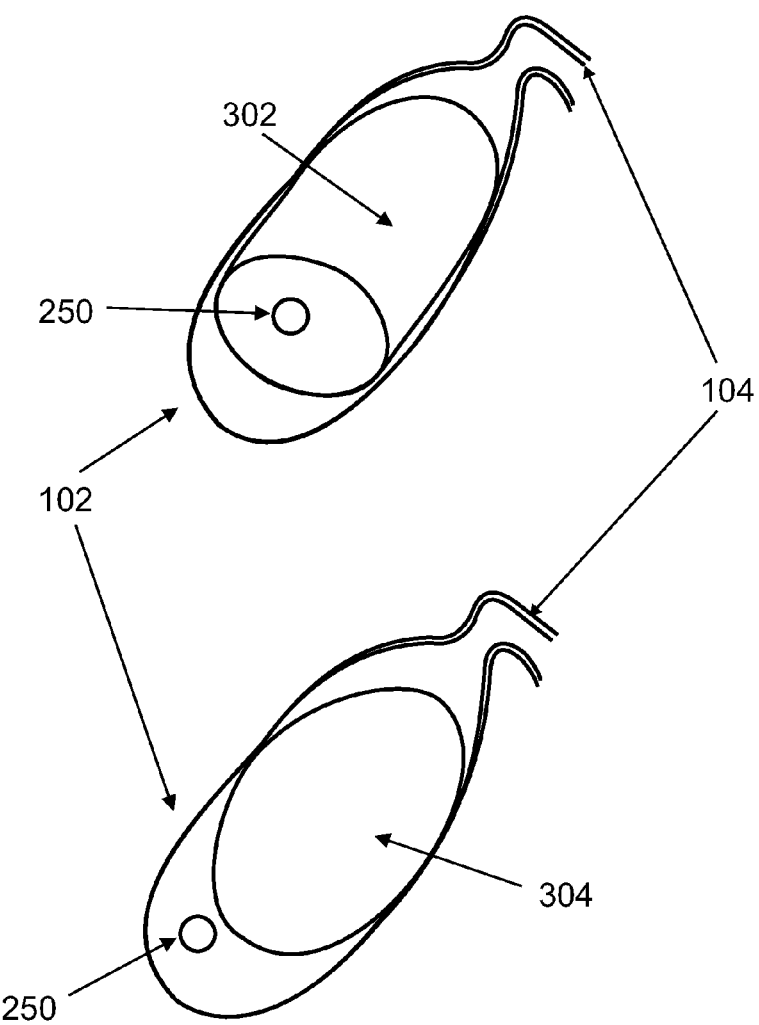

FILTER APPARATUSES AND METHODS OF USING SAME

RELATED APPLICATIONS

This application is a National Phase of PCT Patent Application No. PCT/IL2010/000258 having International filing date of Mar. 25, 2010, which claims the benefit of priority of Israeli Application Serial No. 197800, filed on Mar. 25, 2009. The contents of the above applications are all incorporated herein by reference.

FIELD AND BACKGROUND OF THE INVENTION

The present invention relates generally to treating medical conditions involving ducts and/or body lumens, for example by preventing occlusion of portions of the biliary tree.

Referring to FIG. 1, anatomical features of the biliary tree and its surroundings are shown to provide a reference for the description of the medical conditions, exemplary filter apparatuses and/or methods of ameliorating those conditions. The gall bladder 102 is the eggplant shaped sack which is connected by the cystic duct 104 to the common bile duct 106. The common bile duct 106 represents the "trunk" of the biliary tree and serves as the main conduit for transporting various bodily fluids and/or materials from the liver 116, gall bladder 102 and pancreas 110 through the Sphincter of Oddi 112 and to the small intestine (duodenum) 114.

"Stones" in the gall bladder 102 and bile ducts are found in the entire population, some of them being asymptomatic, and some—symptomatic. In the U.S., 10-15% of the adult population (more than 20 million people) suffer from bile duct stones (about 20% of the population above 65 years of age suffer from gallstones), with more than a million new cases diagnosed annually, and more than 600,000 cholecystectomy procedures performed annually. Patients with gallstones are classified according to three groups: symptomatic, asymptomatic and those suffering from complications caused by the gallstones, such as cholecystitis, pancreatitis or obstructive jaundice.

Asymptomatic patients with gallstones: Many of the patients with gallstones are completely asymptomatic and remain undiagnosed. Gallstones may be detected accidentally during evaluation of other health problems. The increasing diagnosis rate results from increased use of imaging techniques, mainly, but not exclusively, ultrasonic methods. Most of the gallstones are asymptomatic. About 10% of the patients with gallstones will develop symptoms within 5 years of diagnosis, and about 20% of them will develop symptoms within 20 years of diagnosis. The rate of symptom development is maximal during the first years following diagnosis. Entrance of the stones into the bile ducts significantly increases the incidence of complications, such as obstructive jaundice and pancreatitis, up to about 20% in 5 years.

Symptomatic gallstones: The symptoms are the most significant prognostic factors determining the need for therapeutic intervention due to the presence of gallstones. The most common symptom of gallstones is intermittent abdominal pain, located at the right upper quadrant region. The pain typically appears after meals and persists up to several hours. The pain, called "biliary colic", is spasmodic in its nature. It varies in severity, and highly severe pain may require administration of narcotic drugs. Once the gallstones become symptomatic—there is a high probability of further symptom worsening and a high risk of disease progression to a more severe disease, such as acute cholecystitis or acute pancreatitis. About 25% of the patients will develop these complications in 10-20 years.

Complicated gallstones: Cholecystitis, stones in the common bile duct 106 (choledocholithiasis), with or without cholangitis, and pancreatitis are the most common complications of gallstone disease. Acute cholecystitis is caused by cystic duct 104 obstruction by the stones or stone particles and requires hospitalization; this condition may lead to abscess formation, gall bladder perforation, or gall bladder mucocele. Stones left in the gall bladder 102 may lead to chronic bile duct inflammation, scarring, contractures and chronic cholecystitis. A temporary bile duct obstruction causes spasmodic pain, while permanent bile duct obstruction causes inflammation and acute cholecystitis. Passage of the stones from the gall bladder 102 into the cystic duct 104 leads to obstruction of the duct, thus causing the acute clinical syndrome associated with gall bladder 102 drainage obstruction, development of spasmodic pain and acute cholecystitis. The risk for gall bladder 102 cancer is increased by gallstones, but is still very low and does not justify preventive cholecystectomy in asymptomatic patients.

Cholecystectomy eliminates most of the capacity of preserving and secreting bile after meals, and is usually considered to be a physiologically tolerable change. However, this statement is not entirely accurate. A considerable percentage of patients (sometimes up to 40%) will continue suffering from various symptoms similar to the preoperative symptoms, although less prominent and less frequent. Postoperative Duodeno gastric reflux may cause post-cholecystectomy bile gastritis. Furthermore, patients with preoperative gastroesophageal reflux symptoms may suffer from worsening of reflux symptoms following cholecystectomy due to the increased bile content of the reflux fluids; motility changes in the upper Gastro-Intestinal ("GI") tract may also occur after surgery. These changes, as well as impaired lipid absorption, may also contribute to post-cholecystectomy diarrhea. Fecal secondary bile acid levels are increased following cholecystectomy and in colorectal cancer patients, suggesting their involvement in colorectal cancer, as well as contribution of cholecystectomy to the development of colorectal cancer. Increased incidence of colorectal cancer following cholecystectomy has been reported, mainly in the right descending colon, more frequently in women. However, these findings require further investigation and confirmation.

The currently available treatment: gallstone dissolution and extracorporeal shock wave lithotripsy. Gallstone dissolution may be performed by chenoeoxycholic acid or ursodeoxycholic acid, or various solvents (e.g. methyl tert-butyl ether) inserted directly into the gall bladder 102 or the bile ducts using endoscopy. This treatment is often combined with extracorporeal shock wave lithotripsy or endoscopic cholecystectomy techniques. Extracorporeal shock wave lithotripsy involves extracorporeal production of computer focused shock waves by an electromagnetic or ultrasonic source in order to break up the gallstones. The stone fragments are secreted via the biliary tree into the duodenum 114.

Gallstones are suitable for dissolution therapy only if the gall bladder 102 presents at least 50% of the normal contraction capacity, the gallstones are less than 1 cm in diameter, occupy less than 40% of the gall bladder 102 volume, and are non-calcified stones of cholesterol or mixed type.

Less than 30% of all gallstones fulfill these criteria. The treatment causes maximal dissolution of gallstones during the first 6 months, but is not cost-effective after periods longer than 12 months. The treatment is associated with a failure rate of 50% and recurrence rate of 25-50%. The selection requirements for extracorporeal shock wave lithotripsy are identical to those described above for dissolution therapy. The suitable stones are small radiolucent stones smaller than 2 cm in diameter. Passage of the fragments through the cystic duct 104 and the papilla following treatment is painful, usually requiring pain management with narcotics.

Asymptomatic gallstones: Diagnosis of asymptomatic gallstones raises the question whether the patient should be referred to elective cholecystectomy due to a certain risk (2%) for the development of symptoms or complications. Most of the asymptomatic patients prefer to avoid the pain, the expenses and the risks associated with elective surgery, despite the risk of severe complications.

Symptomatic gallstones (periodic biliary colic attacks): The symptomatic patients are at increased risk for the development of complications, thus justifying the indication for cholecystectomy. The common surgical procedure is open cholecystectomy. Elective surgery, if performed during periods devoid of complications, is usually safe, with low mortality rates of only 0.1-0.5%. Since 1988, laparoscopic cholecystectomy is the preferred surgical procedure in view of the short operative time, reduced postoperative pain and discomfort and good cosmetic results. Despite these advantages, about 5% of the laparoscopic procedures are switched, in the course of surgery, to open cholecystectomy, requiring full abdominal opening. In most cases, this is due to the inability to safely identify the gall bladder 102 anatomy or to cope with intraoperative complications.

Endoscopic retrograde cholangiopancreatography ("ERCP"): An imaging technique used for the diagnosis of pancreatic, hepatic and biliary diseases, which can also be used as a therapeutic tool. The endoscope is inserted into the patient's mouth, via the esophagus, the stomach and the upper part of the small intestine. A tube is inserted through the spot into which the bile ducts are emptied, and contrast material is injected through this tube into the bile ducts, followed by a series of X-ray images enabling visualization of the bile ducts. If bile duct stenosis is observed, a stent may be inserted to alleviate stenosis. In order to perform this procedure, catheter sphincterotomy (incision through the Sphincter of Oddi 112) is performed, accompanied by balloon inflation, and finally followed by insertion of the stent into the common bile duct 106. Most of the patients with pancreatic cancer may present with obstruction of the distal part of the biliary tree and jaundice at any stage of their disease. ERCP with sphincterotomy and stent insertion is a therapeutic option providing relief for these patients. At present, EPCR is not used for insertion of stents into the gall bladder 102 itself, or into the proximal bile ducts, such as the cystic duct 104, and the method does not enable treatment of gallstones—especially gallstones located in the gall bladder 102 itself.

Nephrolithiasis is a common disease that is estimated to incur medical costs of $2.1 billion per year in the United States alone. Nephrolithiasis specifically refers to calculi in the kidneys (renal calculi), but renal calculi and ureteral calculi (ureterolithiasis) are often related. Ureteral calculi almost always originate in the kidneys, although they may continue to grow once they lodge in the ureter.

Urinary tract stone disease is likely caused by two basic phenomena. The first phenomenon is supersaturation of the urine by stone-forming constituents, including calcium, oxalate, and uric acid. Crystals or foreign bodies can act as nidi, upon which ions from the supersaturated urine form microscopic crystalline structures. The overwhelming majority of renal calculi contain calcium. Uric acid calculi and crystals of uric acid, with or without other contaminating ions, comprise the bulk of the remaining minority. The second etiology, which is most likely responsible for calcium oxalate stones, is deposition of stone material on a renal papillary calcium phosphate nidus, typically a Randall plaque.

The lifetime prevalence of urinary tract stone disease in the United States is approximately 10%. The annual incidence of urinary tract stones in the industrialized world is estimated to be 0.2%. The likelihood that a white male will develop stone disease by age 70 years is 1 in 8. Stones of the upper urinary tract are more common in the United States than in the rest of the world. Roughly two million patients present on an outpatient basis with stone disease each year in the United States, which is a 40% increase from 1994.

SUMMARY OF THE INVENTION

An aspect of an exemplary embodiment of the invention relates to filter devices for stopping selected structures, such as gall stones or renal calculi, from passing through the filters while still allowing bodily fluids and smaller structures to pass therethrough, in contrast to conventional stents which widen the passageway, allowing even larger structures through than normal which are likely to clog non-stented portions of a lumen. In some embodiments of the invention, the filter devices are adapted to elute pharmaceuticals into the body after implantation. For example, filter devices are provided with a biodegradable coating which releases the pharmaceuticals as the coating degrades. In some embodiments of the invention, the device is bioabsorbable and/or biodegradable and/or biocompatible.

In an embodiment of the invention, filter devices are adapted to prevent potentially problem causing gall stones from leaving the gall bladder. In an embodiment of the invention, the filter device is at least one of a mesh, a spiral or coil and a perforated structure. In an embodiment of the invention, the filter device is designed and/or constructed so that no bio-film grows on it once it is implanted. In an embodiment of the invention, a filter device is provided with a blocking section implanted at least partially in the gall bladder for preventing gall stones from passing into the cystic duct and an anchoring section at least partially positioned in the cystic duct to prevent unwanted movement of the filter device. Optionally, a filter device is implanted entirely within the gall bladder and is provided with an anchoring section which reduces or prevents undesired rotation and/or sinking of the filter device. In some embodiments of the invention, both the blocking section and the anchoring section provide a filtering function to prevent gall stones from passing the cystic duct. In some embodiments of the invention, both the blocking section and the anchoring section provide anchoring function.

In some embodiments of the invention, the filter device is designed to maintain an effective treatment position within the gall bladder and the cystic duct without exerting potentially harmful radial force. The filter device is shaped with enlarged ends with a narrow middle portion between the ends to utilize the natural shape of the anatomy between the gall bladder and the cystic duct, in an embodiment of the invention. The enlarged ends prevent the filter device from moving substantially further into the gall bladder or further into the cystic duct, thereby maintaining its position in between the two without using radial force to hold the filter device in place. In an embodiment of the invention, the filter device has only one enlarged end. Optionally, the enlarged end is on the gall bladder side. Optionally, the enlarged end is on the cystic duct side In some embodiments of the invention, the filter devices are adapted to prevent renal calculi of a predetermined minimum size (radius) from exiting the kidney and moving downstream in the renal system. In some embodiments of the invention, a blocking section is provided to the renal filter device to filter renal calculi in a coiled, spiral or mesh configuration.

Optionally and/or additionally, an anchoring section is provided to the renal filter device for reducing and/or preventing unwanted movement of the renal filter device at the implantation site. In an embodiment of the invention, the anchoring section is a filament extension of the filter device which extends a sufficient length downstream to maintain the filter device in position. In an embodiment of the invention, the filament extension can be said to be axial to the longitudinal axis of the filter device, even if it isn't strictly straight or uniform. For example, the extended filament could be slightly coiled, but still generally extend along the longitudinal axis of the device away from the blocking section.

An aspect of an exemplary embodiment of the invention relates to a method of implanting a filter device in at least a part of the gall bladder for preventing gall stones from lodging in the biliary tree and/or for prevention of gall stone related disease, for example Cholecystitis, Choledocholithiasis, Cholangitis, and pancreatitis. In an embodiment of the invention, the GI tract is accessed by entering through the mouth. An endoscope and/or a guiding wire and/or a catheter is used to navigate the GI tract to the Sphincter of Oddi, in an embodiment of the invention. The Sphincter of Oddi is traversed and the navigation resumes through the common bile duct to the cystic duct. Optionally, a sphincterotomy is performed to traverse the Sphincter of Oddi. In some embodiments of the invention, the filter device is implanted partially in the cystic duct and partially in the gall bladder. Optionally, the filter device is implanted entirely in the gall bladder. In some embodiments of the invention, medical imagine is used to indicate anatomical features and/or to navigate through the patient.

In an embodiment of the invention, the filter device is inserted into the patient in a contracted form. Subsequently, the filter device is expanded at the desired implantation site. Optionally, the filter device expands automatically due to inherent resilience when it is expelled from a catheter which holds it in a contracted/compressed form. Optionally, the filter device expands as a result of its shape memory alloy construction. Optionally, the filter device is expanded using at least one balloon.

Besides the implantation method described above, any other technique leading to the Sphincter of Oddi and/or the gall bladder, such as laparoscopy or open surgery, may be used.

In an embodiment of the invention, a filter device can be removed or is designed to be bio-absorbed at any time.

An aspect of an exemplary embodiment of the invention relates to a method injecting a filter device into at least a part of the gall bladder and/or cystic duct for the prevention of gall stone related diseases without having to implant the filter by traversing the GI tract and the biliary tree. In an embodiment of the invention, the filter device is loaded into an injector. Medical imaging is optionally used to provide guidance for the percutaneous injection and/or delivery of the filter device into at least a part of the gall bladder and/or cystic duct. Upon successful deployment of the filter device, the injector is retracted from the patient.

An aspect of an exemplary embodiment of the invention relates to a method of implanting a renal filter device in at least part of a kidney for the prevention of kidney stone related diseases, such as Nephrolithiasis. In an embodiment of the invention, a catheter is inserted into the urethra of the patient and navigated in the bladder from the urethra and into the ureter. The catheter is urged up the ureter towards the kidney to the implantation site, in an embodiment of the invention. A renal filter device is deployed once the distal end of the catheter has reached the desired location, in accordance with an embodiment of the invention. Once the renal filter device has been deployed at the implantation site, the catheter is retracted from the patient. Optionally, the renal filter device is loaded prior to insertion of the catheter into the urethra. Optionally, the renal filter device is loaded prior to navigation of the catheter into the ureter. Optionally, the renal filter device is loaded into the catheter before the catheter is urged towards the kidney in the ureter. In some embodiments of the invention, medical imaging is used to guide the implantation procedure.

An aspect of an exemplary embodiment of the invention relates to a method of injecting a renal filter device into at least part of a kidney for the prevention of kidney stone related diseases and/or without having to implant the filter by traversing the renal system. In an embodiment of the invention, the filter device is loaded into an injector. Medical imaging is optionally used to provide guidance for the percutaneous injection and/or delivery of the filter device into at least part of a kidney. Upon successful deployment of the filter device, the injector is retracted from the patient.

An aspect of an exemplary embodiment of the invention relates to a method for treating Nephrolithiasis and/or prevention of related ureterolithiasis, without resorting to surgical procedures. In an embodiment of the invention, a renal filter device is implanted into at least a part of the kidney thereby retaining renal calculi of a certain minimum size within the kidney. In an embodiment of the invention, a collecting gel is introduced into the kidney in such a manner as to aggregate the renal calculi into a particular location in the kidney, for example by introducing the gel close to the ureter/kidney junction and pushing the calculi into the calyces. Optionally, the collecting gel is injected into the kidney. Optionally, the collecting gel is introduced into the kidney from a catheter which has transited the renal system. In an embodiment of the invention, shockwave therapy is applied to the collected renal calculi to fracture the calculi into pieces smaller than the certain minimum size being filtered by the renal filtering device. The renal filtering device passes the smaller calculi into the ureter to be flushed out by the natural urine flow. In an embodiment of the invention, the renal filter device and/or the gel are removed and/or are designed to be bio-absorbed and/or biodegradable.

There is thus provided in accordance with an embodiment of the invention, a filter device for implantation in a body lumen, comprising: a blocking section for filtering structures greater than a specified minimum size; and, an anchoring section for preventing unwanted movement of the filter device, wherein the filter device does not apply expansive radial force on a wall of the body lumen.

In an embodiment of the invention, the blocking section and the anchoring section are positioned on either side of a middle portion, respectively, wherein the middle portion has a smaller diameter than the blocking section or the anchoring section.

In an embodiment of the invention, the blocking, middle and anchoring sections substantially conform to the anatomical features of the body lumen such that no radial force is required to maintain the position of the filter device in the body lumen.

Optionally, at least the blocking section is mesh. Optionally, at least the blocking section is a spiral. Optionally, at least the blocking section is a perforated structure.

In an embodiment of the invention, the specified minimum size is 0.6 cm-1.2 cm in the largest dimension. In an embodiment of the invention, the specified minimum size is greater than 1.2 cm in the largest dimension.

In an embodiment of the invention, at least part of the filter is comprised of at least one of the enlarged ends.

In an embodiment of the invention, the entire device is comprised of a single filament. Optionally, the blocking section is a shaped section of the filament. Optionally, the anchoring section is a small diameter filament extending generally axial to the filter device.

In an embodiment of the invention, the blocking section is 1.0 cm-4.5 cm in radius. In an embodiment of the invention, the anchoring section is 0.8 cm-1.2 cm in radius.

In an embodiment of the invention, the device is made from at least one of a metal, a shape memory alloy and a polymer.

In an embodiment of the invention, the device is adapted for eluting a pharmaceutical after implantation.

In an embodiment of the invention, the device is at least one of bioabsorbable and biodegradable.

In an embodiment of the invention, at least one of the blocking section and anchoring section are configured to prevent bio-film growth.

In an embodiment of the invention, the minimum specified size is 3.0 mm-8.0 mm in diameter in the largest dimension.

There is further provided in accordance with an embodiment of the invention, a method of implanting a filter device, comprising: inserting at least one of an endoscope, a guide wire and an elongated tool into a patient's mouth to a duodenum; advancing the at least one of an endoscope, a guide wire and an elongated tool past a Sphincter of Oddi and into a common bile duct; navigating the filter device using the at least one of an endoscope, a guide wire and an elongated tool to a desired implantation site at least partially in the gall bladder; and, implanting the filter device at the desired implantation site at least partially in the gall bladder.

In an embodiment of the invention, the method further comprises performing a sphincterotomy of the Sphincter of Oddi to advance the at least one of an endoscope, a guide wire and a catheter past the Sphincter of Oddi and into the common bile duct.

In an embodiment of the invention, the method further comprises using medical imaging to image at least one of the gall bladder, the cystic duct and the gastro-intestinal tract.

In an embodiment of the invention, implanting includes expanding the filter device at the desired implantation site. Optionally, the desired implantation site includes at least a portion of the gall bladder and at least a portion of the cystic duct. Optionally, the desired implantation site is entirely within the gall bladder.

In an embodiment of the invention, expanding is performed using at least one expansion balloon. Optionally, expanding occurs as a result of a shape memory characteristic of the filter device. Optionally, expanding occurs as a result of a resilience characteristic of the filter device.

There is further provided in accordance with an embodiment of the invention, a method of stabilizing a filter device without exerting potentially harmful radial force, comprising: providing the filter device with an enlarged end on either side of a narrow middle portion; and, implanting the filter device at an implantation site wherein a narrow radius middle portion connects two larger radius end portions such that the filter device cannot move substantially towards either end portion.

There is further provided in accordance with an embodiment of the invention, a method of injecting a filter device into at least a portion of a body lumen, comprising: loading the filter device into an injector; injecting percutaneously the filter device into at least a portion of the body lumen; and, retracting the injector.

In an embodiment of the invention, the method further comprises using medical imaging to provide guidance for the injecting.

In an embodiment of the invention, the body lumen is a gall bladder.

In an embodiment of the invention, the body lumen is a kidney.

There is further provided in accordance with an embodiment of the invention, a method for treatment of Nephrolithiasis, comprising: implanting a renal filter device into at least a part of a kidney thereby retaining renal calculi of a certain minimum size within the kidney; applying shockwave therapy to the collected renal calculi to fracture the calculi into pieces smaller than the certain minimum size being filtered by the renal filtering device; passing through the renal filter device the smaller calculi into the ureter to be flushed out by the natural urine flow; and, removing the filter device from the at least part of a kidney.

In an embodiment of the invention, the method further comprises introducing collecting gel into the kidney in such a manner as to aggregate the renal calculi into a particular location in the kidney, prior to applying shockwave therapy.

In an embodiment of the invention, removing the filter device is achieved by at least one of bio-absorption and bio-degradation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-2F are perspective views of filter embodiments which at least partly extend into the cystic duct from the gall bladder, in accordance with an exemplary embodiment of the invention;

FIGS. 3A-3G are perspective views of filter embodiments which are implanted in the gall bladder, in accordance with an exemplary embodiment of the invention;

DESCRIPTION OF EMBODIMENTS OF THE INVENTION

Figure 1:
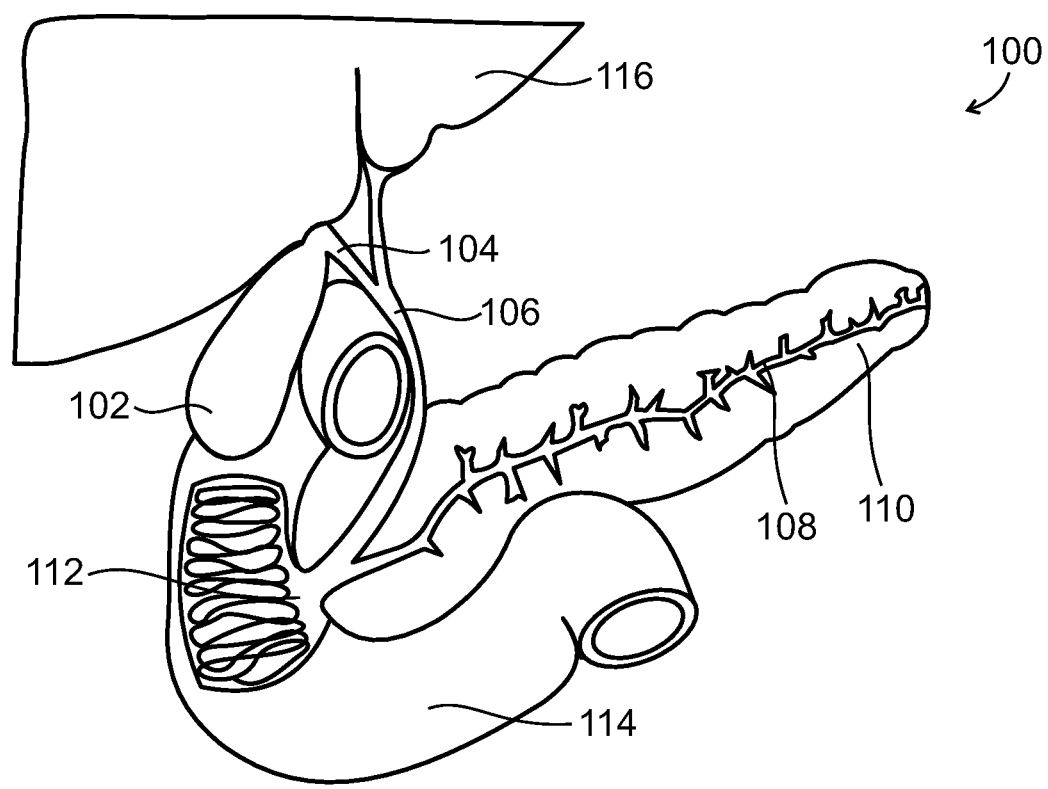
FIG. 1 is an anatomical drawing of at least a portion of the biliary tree, the gall bladder, the pancreas and the duodenum.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments and/or of being practiced or carried out in various ways.

In an embodiment of the invention, the devices described herein spare the patient from suffering and/or surgery, and are intended to prevent the complications of cholecystectomy and anesthesia, operative mortality, postoperative infections (wound infection and other infections), and/or delayed impacts of gall bladder absence (impaired absorption, abdominal pain, etc.) by relieving and/or preventing the symptoms of cholecystitis, pancreatitis or obstructive jaundice, and/or preventing and/or delaying the need for cholecystectomy in patients with gall stones. In some embodiments of the invention, temporary relief, for example of pain induced by gall stones, is provided. In other embodiments of the invention, methods and apparatuses are described for the treatment of disorders caused by renal and ureteral calculi, which often form or do form in the kidneys.

It should be understood that exemplary filter devices described herein are intended to prevent gall stones 250 from passing from the gall bladder 102 into the cystic duct 104 while still allowing for normal flow of bodily fluids and/or secretions through the biliary tree 100 and into the duodenum 114. In some exemplary embodiments of the invention, filtering is achieved without exerting potentially harmful levels of expansive radial force on the walls of the cystic duct 104 and/or gall bladder 102. In some embodiments of the invention, no radial force is applied on the walls of the cystic duct and/or gall bladder.

FIGS. 2A-2F are perspective views of filter embodiments which at least partly extend into the cystic duct 104 from the gall bladder 102, in accordance with an exemplary embodiment of the invention. Referring specifically to FIG. 2A, a filter device 202 is shown which is a mesh-like construction. In an embodiment of the invention, filter device 202 is provided with an anchoring section 214 and a blocking section 216. Generally speaking, blocking section 216 is used to prevent gall stones 250 from passing into the cystic duct 104. Anchoring section is used, in an embodiment of the invention to hold filter 202 in place, as described in more detail below. It should, however, be noted that the use of the terms "blocking" and "anchoring" are used only to give those elements of the filter 202 nomenclature. In some embodiments of the invention, the blocking section 216 also performs anchoring. In some embodiments of the invention, the anchoring section 214 also performs blocking. Optionally, both sections 214, 216 perform anchoring and/or blocking simultaneously. In some embodiments of the invention, size and/or porosity of the anchoring section 214 and/or blocking section 216 are adapted to give the overall filter 202 desired filtering properties.

In an embodiment of the invention, filter device 202 is shaped to maintain position within the gall bladder 102 and cystic duct 104 in order to render effective filtering, without applying potentially harmful radial force. In an embodiment of the invention, anchoring section 214 and blocking section 216 are wider in diameter than the middle of filter device 202 in order to take advantage of the shape of the anatomical features at the interface between the gall bladder 102 and the cystic duct 104. More specifically, the radius of the duct immediately between the gall bladder 102 and the cystic duct 104 narrows towards its middle and is narrower than either the cystic duct or the gall bladder in any normal human being. By providing filter device 202 with ends that have a larger radius than the duct between the gall bladder 102 and the cystic duct 104, the device is maintained in position without being able to substantially move either towards the gall bladder 102 or cystic duct 104. In an embodiment of the invention, the blocking section 216 is approximately 1.0 cm-4.5 cm in radius. In an embodiment of the invention, anchoring section 214 is approximately 0.8 cm-1.2 cm in radius. By using this technique for stabilizing the filter device 202, virtually no radial force, if any, is used.

In an embodiment of the invention, blocking section and anchoring section are separately formed elements which are connected together to form the filter device. In some embodiments of the invention, the sections are connected by at least a single filament. Optionally, the sections are connected by a plurality of filaments. In some embodiments of the invention, a net connects the two sections. Optionally, the net is a mesh net. In some embodiments of the invention, the sections are attached directly together, for example by laser welding, without an intervening connecting piece. It should be understood that virtually any suitable connector cold be used, which allows the filter device to be conformable to the body lumen anatomy and/or which maintains the relative spatial relationship between the blocking and the anchoring section and/or which is suitable for filtering structures of a certain size while allowing structures smaller than that certain size to pass downstream.

In some embodiments of the invention, the entre filter device is constructed of a single filament, which is shaped to form the coiled or spiraled blocking section and/or the anchoring section, whether straight, or gently curved, or the like. In some embodiments of the invention, the anchoring section 214 is comprised of a long, small radius filament which extends from the cystic duct 104 towards, to and/or past the common bile duct. Optionally, the filament provides anchoring to the filter 202 by extending into the duodenum. In an embodiment of the invention, the filament extension can be said to be axial to the longitudinal axis of the filter device, even if it isn't strictly straight or uniform. For example, the extended filament could be slightly coiled, but still generally extend along the longitudinal axis of the device away from the blocking section.

In an embodiment of the invention, the mesh structure is designed to prevent gall stones 250 whose minimum dimension is greater than 0.9 cm-1.1 cm from passing through filter device 202 but is not of such tight configuration to prevent bodily fluids from passing therethrough. Optionally, gall stones whose minimum dimension is 1.2 cm or greater are prevented from passing through filter device 202. In an embodiment of the invention, the pores of the mesh are slot, circular, oblong, quadrilateral or other similar shapes which can be sized accordingly.

The mesh or mesh-like material is selected to be biocompatible and/or bio-absorbable, in an exemplary embodiment of the invention. Optionally, the mesh is a polymer material. In some embodiments of the invention, the mesh is metal. Optionally, the mesh is a shape memory alloy such as nickel titanium, also known as Nitinol®. In some embodiments of the invention, the mesh is coated, for example with Teflon® or other similarly inert or highly non-reactive coating. Optionally, the mesh and/or the coating is adapted to elute a substance, for example a pharmaceutical.

In some embodiments of the invention, the porosity of the mesh is small enough to prevent the passage of selectively sized gall stones 250 but is large enough to prevent bio-film growth over the device. For example, the pores of the mesh are 0.9 cm cm±0.2 cm in diameter. In an embodiment of the invention, the mesh is closed-cell. In some embodiments of the invention, the mesh is open-cell. In some embodiments of the invention, the mesh is a combination of open-cell and closed-cell portions, wherein the anatomy that the filter device is intended to conform to determines open-cell and/or closed-cell configurations of the mesh. In some embodiments of the invention, choice of construction material also factors into the prevention of bio-film growth, for example metal, polymer and/or shape memory materials could be used. Optionally, an anti-bio-film agent, like an antibiotic, is eluted from and/or covers the mesh.

In some embodiments of the invention, the filter is shaped to allow for slight movement within the implantation site in order to prevent or delay bio-film growth via device motion. Optionally, the filter is moved by movement of the gall bladder and/or the surroundings of the implantation site itself. In an embodiment of the invention, the filter moves and/or flexes to cause any accumulation of bio-film to break, crack and/or at the very least create openings through the bio-film such that natural secretions of the gall bladder continue to flow. In an embodiment of the invention, specific filter configurations are chosen for bio-film prevention, for example that shown in FIG. 2F, whose "rabbit ear" configuration permits the ears to move apart during movement of the filter, causing any accumulated bio-film to break, crack and/or split. Optionally, movement and/or flexing of the filter occurs only in a location where bio-film accumulation is likely to occur, for example on the side of the filter closer to the gall bladder than the cystic duct In some embodiments of the invention, bio-film growth is cleared and/or stunted and/or prevented by natural secretions of the bile duct which are allowed to flow normally even with a filter device implanted. It is noted that an implanted stent would actually widen the cystic duct, thereby slowing the flow therethrough of bile and degrading the bile's ability to combat bio-film.

FIG. 2B is a filter device 204 which exhibits a coiled or spiral construction instead of a mesh construction, in accordance with an exemplary embodiment of the invention Like the mesh embodiments, the spiral shape serves to retain gall stones 250 in the gall bladder 102 while still permitting bodily fluids to drain from the gall bladder 102 into the cystic duct 104 and biliary tree 100, downstream. Materials used for construction of filter device 204 are metal, shape memory alloy and/or polymers in some embodiments of the invention.

In an embodiment of the invention, the winds of the spiral are spaced apart sufficiently to make it harder for a bio-film to grow on filter device 204.

Stabilization of filter device 204 without exerting substantial radial force is accomplished by providing enlarged ends on either side of filter device 204 while maintaining a narrower middle portion, in accordance with an exemplary embodiment of the invention.

It should be understood that two basic types of construction (mesh and spiral/coil) have been described for the filter devices which occupy at least a portion of both the gall bladder 102 and the cystic duct 103. In some embodiments of the invention, a perforated structure (e.g. a sheet located on the gall bladder 102 side of a filter device with perforations) is used as the filter. Different shapes can be formed using these types of construction which still provide the filtering quality of the devices and still maintain their effective treatment locations. For example, filter devices 206, 208 and 212 in FIGS. 2C, 2D and 2F, respectively, show mesh devices with different filter shapes but which still are effective for preventing gall stones 250 from entering the cystic duct 104 and which have enlarged ends and a narrow middle potion for stabilization without much radial force. Filter device 210 of FIG. 2E shows a different spiral shape than that of filter device 204 but which is still effective to filter gall stones 250 of selected sizes and which maintains its position between the gall bladder 102 and the cystic duct 104. FIGS. 2C and 2F have tail-like shapes for the anchoring section which are sufficient, in some embodiments of the invention, for providing the necessary anchoring properties desired. Optionally, the tail is substantially straight, for example as shown in FIG. 2C. Optionally, the tail has at least one curve and/or a loop at the end for safety (to prevent the end of the tail from puncturing and/or abrading the lumen wall). The shapes shown in FIGS. 2A-2F are merely representative and other filter device configurations could be used, for example with different conical shapes on either side of the device, flat shapes on the gall bladder 102 side, spherical shapes on either side, pear shapes on either side, concave shapes (like in FIG. 2E) and the like. In addition, blocking section and anchoring section configurations described herein are optionally interchangeable and/or mix and match.

FIGS. 3A-3G are perspective views of filter embodiments which are implanted entirely or substantially in the gall bladder 102, in accordance with an exemplary embodiment of the invention. Generally, in an embodiment of the invention, optional construction materials for the devices depicted in FIGS. 3A-3G are the same as those for devices depicted in FIGS. 2A-2F. In some embodiments of the invention, at least a portion of the devices of FIGS. 3A-3G are mesh and/or are spiraled. In some embodiments of the invention, mesh porosities and/or shapes described with respect to embodiments depicted in FIGS. 2A-2F are applicable to the embodiments of FIGS. 3A-3G.

FIG. 3A shows a cup shaped filter device 302 which is implanted entirely within the gall bladder 102, in an exemplary embodiment of the invention. It can be seen that gall stones 250 moving towards the cystic duct 104 would become trapped in the filter device 302, preventing the gall stones 250 from migrating into the cystic duct 104 and/or further downstream in the biliary tree. In an exemplary embodiment of the invention, filter device 302 is sized to occupy the full radius of the gall bladder 102 to prevent a gall stone 250 from passing around filter device 302 and escaping from the gall bladder 102.

FIG. 3B shows a filter device 304 which is essentially a mass lodged within the gall bladder 102 which is capable of blocking gall stones from exiting the gall bladder but which still permits the flow of natural body fluids into the biliary tree. In an embodiment of the invention the filter device 304 is at least partially mesh.

Figure 3C:
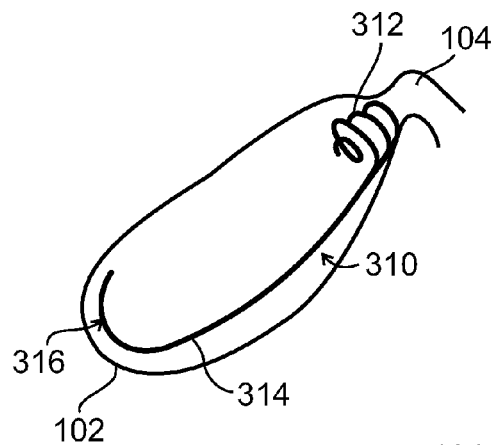
Figure 3D:
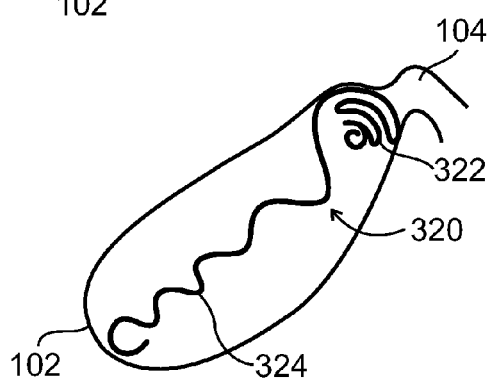
Figure 3E:
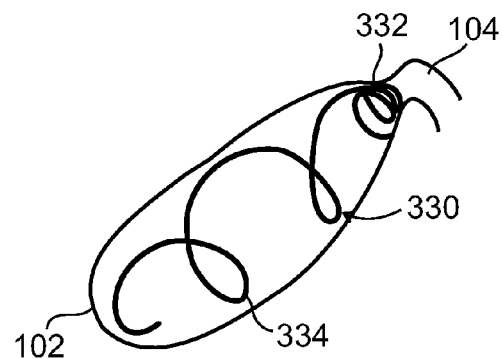
Figure 3F:
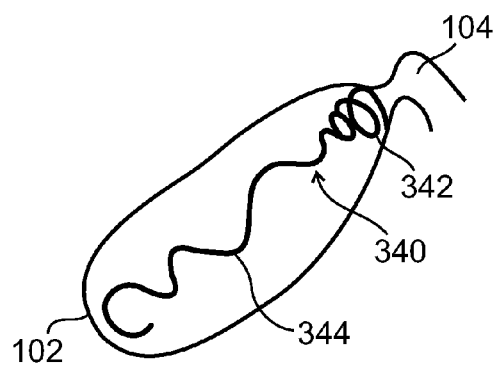
Figure 3G:
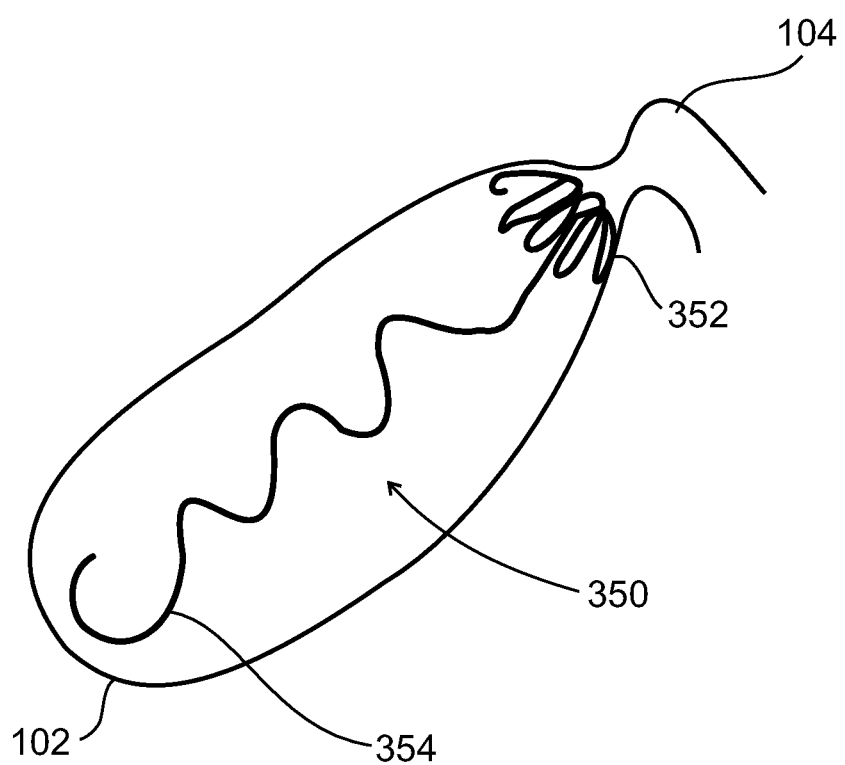

FIGS. 3C-3G depict various embodiments which are at least substantially implanted in the gall bladder 102, in accordance with an exemplary embodiment of the invention. FIGS. 3C-3F show filter devices 310, 320, 330, and 340 which include a spiral or coil type blocking section 312, 322, 332, and 342, respectively. FIG. 3G shows a filter device 350 with a mesh-type blocking section 352. It can be seen that these blocking sections 312, 322, 332, 342, 352 each have a slightly different shape wherein some taper towards the cystic duct 104, some taper away from the cystic duct 104, or both sides taper from a larger midsection of the blocking section, for example in FIG. 3F. Of particular note is the anchoring sections 314, 324, 334, 344, 354 of these filter devices, wherein elongated anchoring sections which extend from the blocking section away from the cystic duct are used to prevent unwanted motion of the filter devices, including rotation (where the filter device might rotate thereby rotating the blocking section away from the cystic duct) and/or sinking, where the blocking section 312, 322, 332, 342, 352 might move away from the cystic duct 104 and allow a gall stone 250 to "sneak" around the filter device and into the cystic duct 104. In an embodiment of the invention, rotation is prevented by having an anchoring section which extends away from the cystic duct 104 a sufficient length to prevent rotation away from the cystic duct to such a degree that a gall stone 250 could pass the blocking section. Sinking is prevented, in an embodiment of the invention, by having an anchoring section of sufficient length that any movement of the blocking section away from the cystic duct 104 causes the distal end 316 of the anchoring section to bump against the wall of gall bladder 102, stopping the sinking movement away from the cystic duct 104. In an embodiment of the invention, at least a portion of the filter devices is lodged into the part of the cystic duct 104 proximal to the gall bladder 102 in order to anchor the filter devices.

Figure 4:
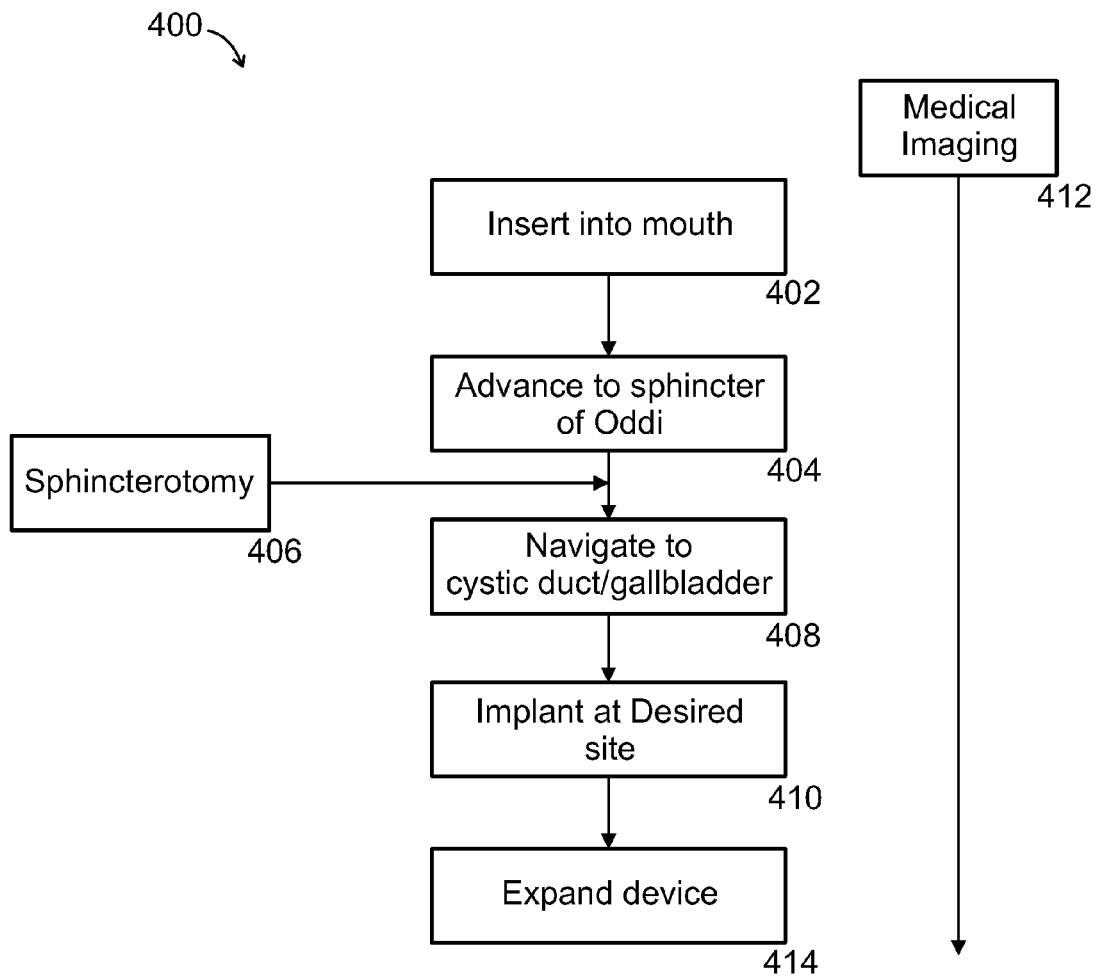
FIG. 4 is a flowchart depicting a method of implanting a filter in the gall bladder and/or the cystic duct, in accordance with an exemplary embodiment of the invention.

FIG. 4 is a flowchart 400 depicting a method of implanting a filter in the gall bladder 102 and/or the cystic duct 104, in accordance with an embodiment of the invention. In an embodiment of the invention, implantation may be performed without general anesthesia and is considered to be minimally invasive. In an embodiment of the invention, a filter device is inserted (402) into the GI tract via the mouth, through to the esophagus, through to the stomach and then into the duodenum 114. Navigation and/or insertion are accomplished using an endoscope and/or a guiding wire and/or an elongated tool, such as a catheter, as chosen by the attending medical professional performing the procedure, in an embodiment of the invention.

The filter device is advanced (404) via the Sphincter of Oddi 112 into the common bile duct 106, in an exemplary embodiment of the invention. A sphincterotomy (406) of the Sphincter of Oddi 112 is performed, if required and/or desired, similarly to the method commonly used in endoscopy and ERCP. The filter device is implanted (410) at a desired implantation site by navigating (408) the filter device from the common bile duct 106 through to the cystic duct 104 and/or the gall bladder 102. Contrast material in used order to image (412) the gall bladder 102 and/or the cystic duct 104 and/or the gastro-intestinal tract, in some exemplary embodiments of the invention. Optionally, other commonly available imaging techniques are used for the implantation, for example X-ray and/or ultrasound.

In an exemplary embodiment of the invention, the filter device is inserted (402) in to the patient in a contracted form. In some embodiments of the invention, the filter device expands (414) to its intended size and shape upon arrival at the desired site of implantation. In some embodiments of the invention, the filter device expands (414) as a consequence of its own spring-like behavior, for example upon deployment from a catheter which was used to pass the filter device to the cystic duct 104 and/or gall bladder 102, the device springs into designed shape and size once the catheter is no longer holding the filter device in a contracted state. Optionally, the filter device expands (414) as a result of its shape memory characteristic. In some embodiments of the invention, an expansion balloon is used to expand (414) the filter device. Due to the special anatomic structure of the cystic duct 104 in the gall bladder region, more than one balloon and/or one balloon inflation may be used, for example, using a flexible balloon for initial inflation and a rigid and/or a semi-rigid balloon for filter device fixation.

Besides the implantation method described above, any other technique leading to the Sphincter of Oddi 112 and/or the gall bladder 102, such as laparoscopy or open surgery, may be used.

In an embodiment of the invention, a filter device can be removed or is designed to be bio-absorbed at any time.

In some embodiments of the invention, medical imaging is used for guiding the navigation of the biliary tree and/or implantation of the filter device at the correct implantation site. Optionally, a scope is used to provide imaging. Optionally, x-ray is used to provide imaging. Optionally, ultrasound is used to provide imaging.

Figure 5A:
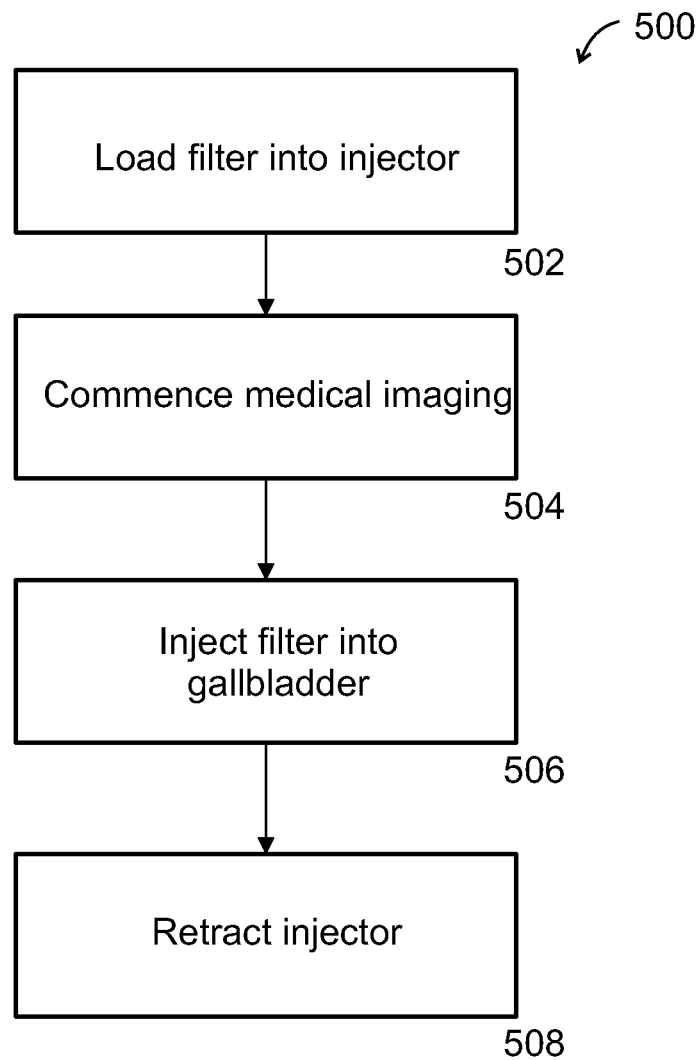
FIG. 5A is a flowchart depicting a method of injecting a filter into the gall bladder and/or cystic duct, in accordance with an exemplary embodiment of the invention.
Figure 5B:
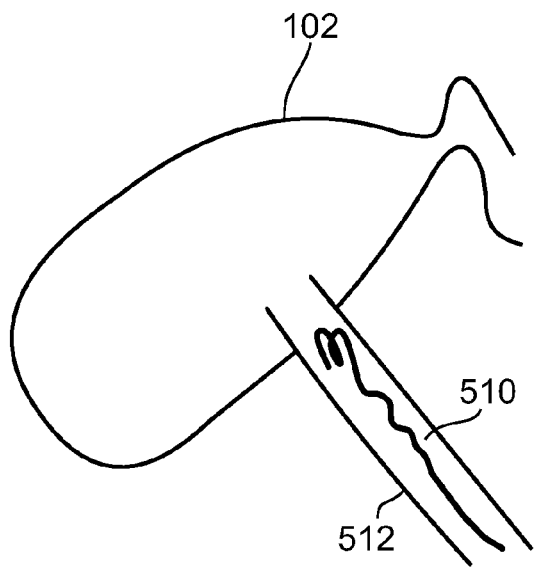
FIG. 5B is a conceptual view of a filter being injected into the gall bladder, in accordance with an exemplary embodiment of the invention.

FIG. 5A is a flowchart 500 depicting a method of injecting a filter into the gall bladder 102 and/or cystic duct 104, in accordance with an exemplary embodiment of the invention. In an embodiment of the invention, a filter to be implanted in the gall bladder 102 is loaded (502) into an injector. Medical imaging (504) is used to guide injection (506) into the gall bladder 102, in an exemplary embodiment of the invention. Injection (506) is carried out by penetration of the injector percutaneously and into the gall bladder 102, wherein the filter device is ejected from the injector and into the gall bladder 102, in an embodiment of the invention. Once the filter device has been injected (506) into the gall bladder 102, the injector is retracted (508) from the patient. FIG. 5B is a conceptual view of a filter 510 being injected into the gall bladder 102 from an injector 512, in accordance with an exemplary embodiment of the invention.

In an embodiment of the invention, the orientation of the injected (506) filter device is preset during loading (502) such that upon injection, the injector is positioned in manner so that upon expulsion of the filter device from the injector, the filter device portion which should be distal from the injector is the first part of the filter device that leaves the injector. In some embodiments of the invention, the distal end of the injector and/or a catheter used for implantation is marked to be detectable by medical imaging so that during the injection and/or implantation process the attending medical professional sees from the medical imaging the precise location where the filter device will be deployed with respect to the patient's anatomy. In some embodiments of the invention, the implant is not pushed out of the implantation catheter or injector, but is pulled out by an opposing device such a tweezers.

Figure 6:
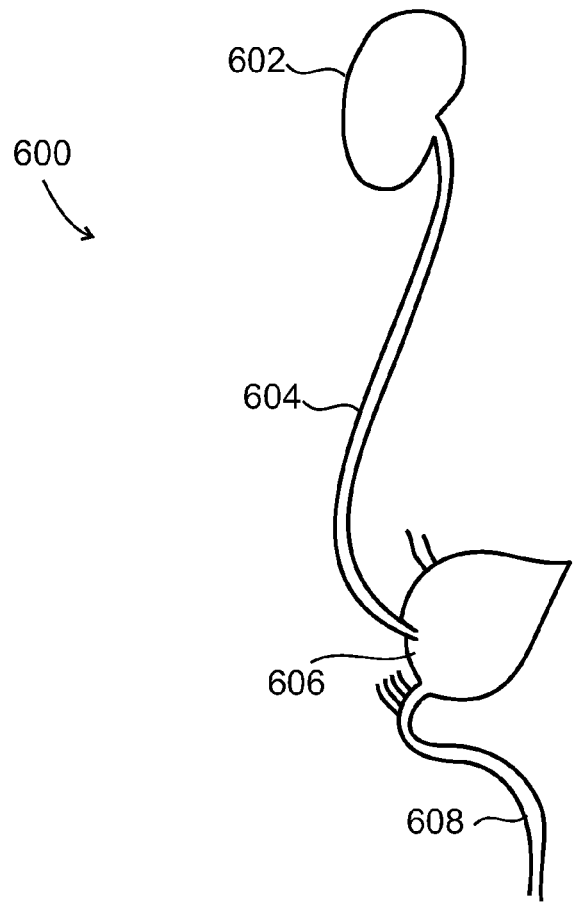
FIG. 6 is an anatomical drawing of at least a portion of the renal system, including the kidney, the ureter and the urinary bladder.

FIG. 6 is an anatomical drawing 600 of at least a portion of the renal system, including the kidney 602, the ureter 604, the urinary bladder 606 and the urethra 608.

As described above in the Background section, renal calculi often migrate from the kidney 602 into the ureter 604 and become lodged causing or contributing to urinary tract stone disease. FIGS. 7A-7D are perspective views of renal filter embodiments 710, 720, 730, 740 which are implanted at least partially in a kidney 602 to prevent certain sized renal calculi from migrating into the ureter 604, in accordance with an exemplary embodiment of the invention. In an embodiment of the invention, filter devices 710, 720, 730, 740 are provided with blocking sections 712, 722, 732, 742, respectively, which are adapted to retain certain sized renal calculi within the kidney 602. Blocking sections 712, 732 are coiled or spiral configuration, similar to those shown and described with respect to FIGS. 2B, 2E and FIGS. 3C-3F. Blocking sections 722, 742 are mesh, similar to those shown in FIGS. 2A, 2C, 2D, 2F and FIGS. 3A, 3B, and 3G. In an embodiment of the invention, renal filter devices do not apply potentially harmful radial force on the walls of the kidney and/or ureter.

In an embodiment of the invention, the blocking section of renal filter devices are adapted to prevent renal calculi larger than 3.0 mm in diameter in the largest dimension from passing into the ureter 604. Optionally, renal calculi larger than 4.0 mm in diameter are prevented from passing into the ureter 604. Optionally, renal calculi larger than 5.0 mm in diameter are prevented from passing into the ureter 604. Optionally, renal calculi larger than 6.0 mm in diameter are prevented from passing into the ureter 604. Optionally, renal calculi larger than 8.0 mm in diameter are prevented from passing into the ureter 604.

Figure 7A:
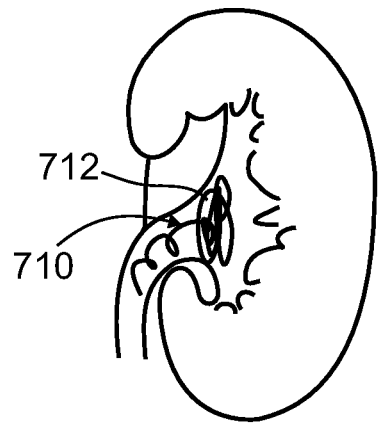
FIGS. 7A-7D are perspective views of filter embodiments which are implanted at least partially in a kidney, in accordance with an exemplary embodiment of the invention.
Figure 7B:
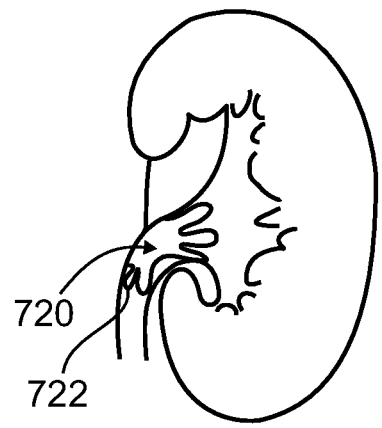
Figure 7C:
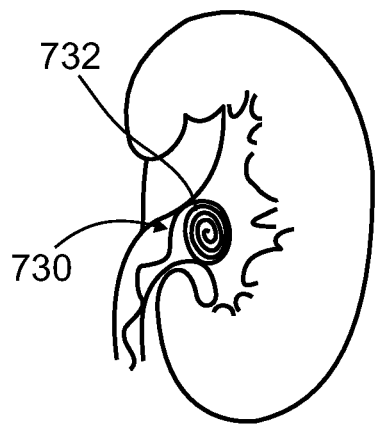
Figure 7D:
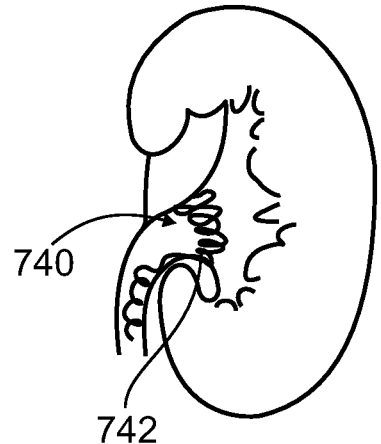

In some embodiments of the invention, renal filter devices are provided with an anchoring section, for example the devices depicted in FIGS. 7A, 7C and 7D. In an embodiment of the invention, the device 720 in FIG. 7B does not have a distinct anchoring section, but has an oversized blocking section which also performs an anchoring function, above and beyond that of the blocking sections of other shown embodiments. The blocking sections and anchoring sections for different embodiments can be mixed and matched in some embodiments of the invention, for example the blocking section of FIG. 7A could be matched with the anchoring section of FIG. 7C.

It should be noted that not all humans have kidneys that are the same size. In adults, the kidney sizes can vary as much as 30% from person to person. As a result, it is conceived that a range of filter device sizes is provided, the size chosen for implantation depending on the individual anatomy of the patient. In some embodiments of the invention, a kit containing various sized filter devices is provided to the medical professional carrying out the implantation procedure to allow for variations in patient kidney sizes.

Figure 8:
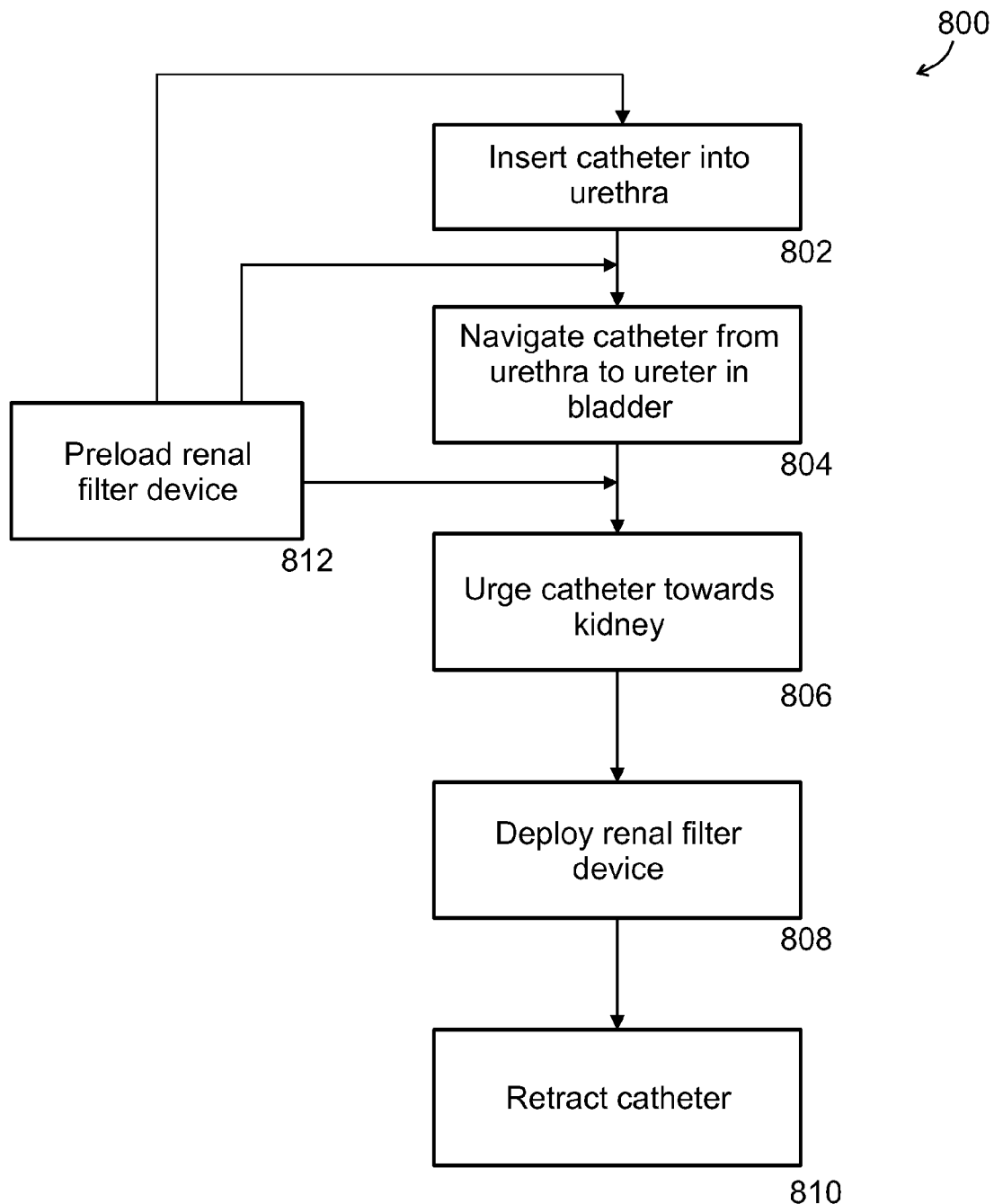
FIG. 8 is a flowchart depicting a method of implanting a filter in the kidney and/or ureter, in accordance with an exemplary embodiment of the invention.

FIG. 8 is a flowchart 800 depicting a method of implanting a filter in the kidney and/or ureter, in accordance with an exemplary embodiment of the invention. A catheter is inserted (802), in an embodiment of the invention, into the urethra 608 and through to the bladder 606, where the catheter is navigated (804) in the bladder 606 from the urethra 608 and into the ureter 604. The catheter is urged (806) towards the kidney 602 in the ureter 604 until the distal end (the part farthest into the body) of the catheter is proximal to the desired implantation site. A renal filter device is advanced through the catheter and deployed (808) at the implantation site by ejecting it from the catheter, in an exemplary embodiment of the invention. Optionally, the renal filter device is preloaded (812) in the distal end of the catheter prior to insertion (802) or after insertion (802) but before navigating (804) or before urging (806). In an embodiment of the invention, the catheter is retracted (810) from the patient's body after renal filter device deployment (808). In some embodiments of the invention, medical imaging is used for guiding the navigation of the renal system and/or implantation of the filter device at the correct implantation site. Optionally, a scope is used to provide imaging. Optionally, x-ray is used to provide imaging. Optionally, ultrasound is used to provide imaging.

Figure 9:
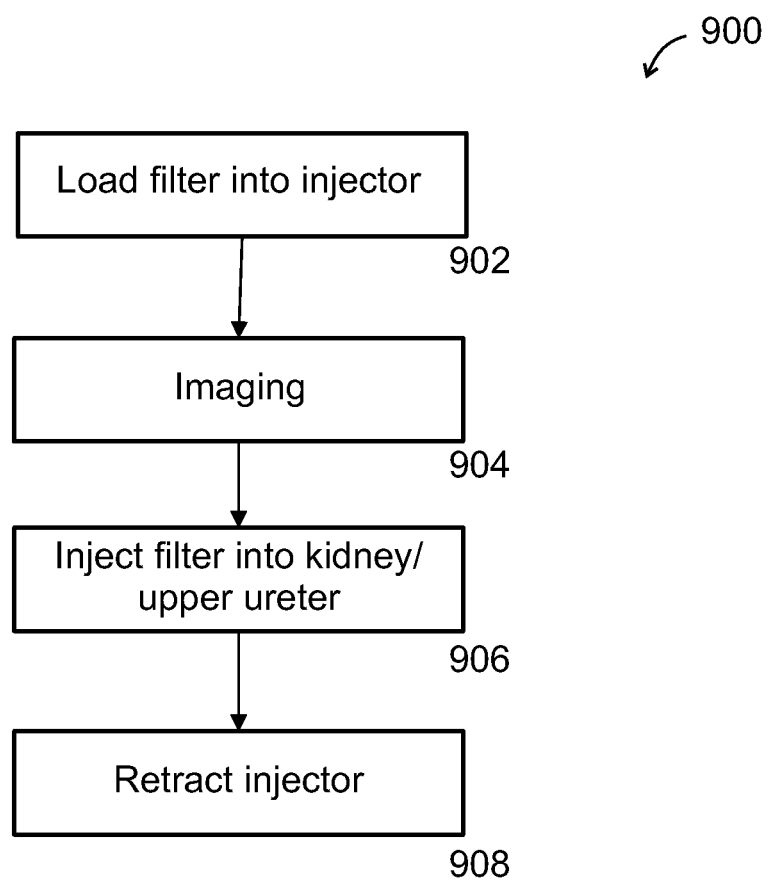
FIG. 9 is a flowchart depicting a method of injecting a filter into the kidney, in accordance with an exemplary embodiment of the invention; and, FIG. 10 is a flowchart depicted a method of treating Nephrolithiasis, in accordance with an exemplary embodiment of the invention.

FIG. 9 is a flowchart 900 depicting a method of injecting a filter into the kidney 602 and/or upper ureter 604, in accordance with an exemplary embodiment of the invention. In an embodiment of the invention, a filter to be implanted in the kidney 602 and/or upper ureter 604 is loaded (902) into an injector. Medical imaging (904) is used to guide injection (906) into the kidney 602 and/or upper ureter 604, in an exemplary embodiment of the invention. Injection (906) is carried out by penetration of the injector percutaneously and into the kidney 602 and/or upper ureter 604, wherein the filter device is ejected from the injector and into the kidney 602 and/or upper ureter 604, in an embodiment of the invention. Once the filter device has been injected (906) into kidney 602 and/or upper ureter 604, the injector is retracted (908) from the patient. In an embodiment of the invention, filter device orientation upon injection deployment is carried out in any of the manners described above with respect to FIG. 5A.

Figure 10:
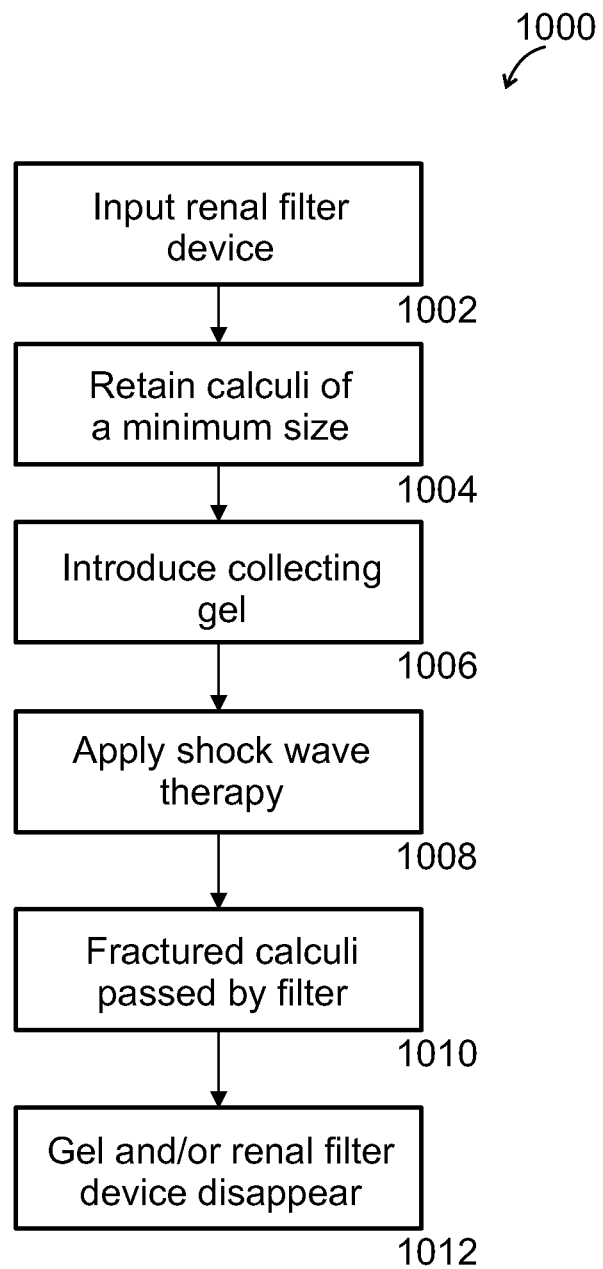

FIG. 10 is a flowchart 1000 depicting a method for treating Nephrolithiasis, in accordance with an exemplary embodiment of the invention. In an embodiment of the invention, renal calculi of a predetermined minimum size are retained (1004) in the kidney by an implanted (1002) renal filter device 710, 720, 730, 740. Optionally, a biocompatible and/or bioabsorbable and/or biodegradable gel is introduced (1006) into the kidney to push the renal calculi to one side of the kidney. Shockwave therapy is applied (1008) to the aggregated renal calculi in order to fracture them into smaller pieces, which are smaller than the predetermined minimum size of the filter device 710, 720, 730, 740 and which therefore can be passed (1010) out of the body in the urine without risk of lodging in the ureter. In an embodiment of the invention, the smaller pieces which are allowed to pass (1010) are small enough size so that they can be passed (1010) painlessly and/or without blocking something downstream. Optionally, the renal filter device 710, 720, 730, 740 is bioabsorbable and/or biodegradable and after a period of time after the treatment the device disappears (1012) from the implantation site.

In an embodiment of the invention, the renal filter device is adapted to convey and/or amplify an applied shockwave and/or vibration applied (1008) to fracture renal calculi.

In some embodiments of the invention, dimensions and/or construction materials given with respect to one embodiment are applicable to other embodiments of filter devices, for example dimensions given with respect to filter 202 can be applied to filter 204. It should also be noted that features described, including dimensions and/or construction materials, with respect to the devices of FIGS. 2A-2F are also applicable to the devices of FIGS. 3A-3G and FIGS. 7A-7D. For example, all devices described herein are optionally bioabsorbable and/or biocompatible and/or biodegradable. As another example, all of the devices described herein can be adapted to elute pharmaceuticals with approximate preset dosages for approximate preset durations.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A filter device for implantation wholly within a gall bladder, comprising:
    a mesh or undulating wire formed into a self-expanding concave filtering blocking section tapering away from a center of the filter device and having a porosity selected to selectively block the passage of gall stones with a dimension greater than a specified minimum size; and,
    a resilient anchoring section which extends the length of the gall bladder from the blocking section located near a cystic duct opening of the gall bladder to a portion of the gall bladder substantially opposite the opening such that said length is sufficient to prevent movement of the blocking section away from said cystic duct opening of the gall bladder by a distal end of the anchoring section contacting said opposite portion and configured to be longer than and with a smaller radial dimension than the blocking section and terminating in a curved or looped end for a traumatic resting against said opposite portion,
    wherein the filter device is sized to wholly fit within a gall bladder and does not apply expansive radial force on a wall of the gall bladder for anchoring the device.

2. A filter device according to claim 1, wherein at least the blocking section is mesh.

3. A filter device according to claim 1, wherein the specified minimum size is 0.6 cm-1.2 cm in the largest dimension.

4. A filter device according to claim 1, wherein the specified minimum size is greater than 1.2 cm in the largest dimension.

5. A filter device according to claim 1, wherein at least part of the filter is comprised of at least one enlarged end.

6. A filter device according to claim 1, wherein the blocking section is a shaped section of the filament.

7. A filter device according to claim 1, wherein the anchoring section is a small diameter filament extending generally axial to the filter device.

8. A filter device according to claim 1, wherein the blocking section is 1.0 cm-4.5 cm in radius.

9. A filter device according to claim 1, wherein the anchoring section is 0.8 cm-1.2 cm in radius.

10. A filter device according to claim 1, wherein the minimum specified size is 3.0 mm-8.0 mm in diameter in the largest dimension.

11. A filter device according to claim 1, wherein the anchoring section distal end is curved near the portion of the gall bladder substantially opposite the opening.

12. A method of implanting a filter device of claim 1, comprising:
    inserting at least one of an endoscope, a guide wire and an elongated tool into a patient's mouth to a duodenum;
    advancing the at least one of an endoscope, a guide wire and an elongated tool past a Sphincter of Oddi and into a common bile duct;
    navigating the filter device using the at least one of an endoscope, a guide wire and an elongated tool to a desired implantation site at least partially in the gall bladder; and, implanting the filter device at the desired implantation site wholly within in the gall bladder, wherein the anchoring section of the filter device is implanted to extend the length of the gall bladder from the blocking section of the filter device located near the cystic duct opening to a wall substantially opposite the cystic duct, thereby mechanically preventing the blocking section from migrating in the gall bladder away from the cystic duct and wherein the filter device does not does not apply expansive radial force to the wall of the gall bladder in order to achieve anchoring.

* * * * *